United States Patent [19]

Azuma

[11] Patent Number: 4,565,830
[45] Date of Patent: Jan. 21, 1986

[54] METHOD OF AMELIORATING THE SUBJECTIVE SYMPTOMS AND OBJECTIVE SIGNS IN CONGESTIVE HEART FAILURE

[76] Inventor: Jun-ichi Azuma, 13-14, Momoyamadai 1-cho, Sakai, Osaka, Japan, 590-01

[21] Appl. No.: 451,837

[22] Filed: Dec. 21, 1982

[30] Foreign Application Priority Data

Dec. 22, 1981 [JP] Japan ............................. 56-207766

[51] Int. Cl.$^4$ ........................................ A61K 31/185
[52] U.S. Cl. ................................................. 514/553
[58] Field of Search ...................... 424/315; 514/553

[56] References Cited

U.S. PATENT DOCUMENTS

| 3,658,966 | 4/1972 | Tsunoo et al. | 424/315 |
|---|---|---|---|
| 3,725,553 | 4/1973 | Giotti et al. | 424/315 |
| 3,789,068 | 1/1974 | Ito et al. | 424/315 |
| 3,790,672 | 2/1974 | Giotti et al. | 424/315 |

OTHER PUBLICATIONS

Braunwald et al., Ed., Congestive Heart Failure, pp. 1-3.
Kramer et al., "Effect of Taurine on Calcium Paradox and Ischemic Heart Failure", American Journal of Physiology (Feb. 1981).
Huxtable et al., "Taurine Concentrations in Congestive Heart Failure", Science, vol. 184 (Jun. 1974), pp. 1187, 1188.
Dietrich et al., "Comparison Between Ouabain and Taurine on Isolated Rat and Guinea-Pig Hearts in Low Calcium Medium", Life Sciences, vol. 10, Pt. I, pp. 499-507 (1971).
Parmley, "Pathophysiology of Congestive Heart Failure" The American Journal of Cardiology (Jan. 11, 1985) pp. 9A-17A.
Francis, Gary S., "Neurohumoral Mechanisms Involved in Congestive Heart Failure" The American Journal of Cardiology (Jan. 1985) pp. 15A-16A.
Sonnenblick, Edmund H. et al., "New Positive Inotropic Drugs for the Treatment of Congestive Heart Failure" (Jan. 1985) pp. 41A-42A.
Nayler, Winifred G., "The Role of Calcium in the Ischemic Myocradium" American Journal of Pathology (1981) pp. 262-269.
Durrer, D. et al., "Past and Future of Calcium Paradox" European Heart Journal (1983) pp. supplement 1-2.
Baker, J. E. et al., "The Temperature-Sensitivity of Slow Channel Calcium Blockers in Relation to Their Effect Upon the Calcium Paradox" European Heart Journal (1983) pp. supplement H 97.
Lomsky, M. et al., "The Calcium Paradox and its Protection by Hypothermia in Human Myocardium" European Heart Journal (1983) pp. Supp. H 139-142.
Chem. Abst. 30, 8399(8) (1936)—Sterner et al.
Chem. Abst. 47, 6098(h) (1953)—Glaessner.
Chem. Abst. 93, 5,350(u) (1980)—Swynghedauw et al.
Chem. Abst. 94, 63,316(u) (1981)—Kramer et al.
Chem. Abst. 95, 40,454u (1981)—Lombardini et al.

Primary Examiner—Douglas W. Robinson
Attorney, Agent, or Firm—Pahl, Lorusso & Loud

[57] ABSTRACT

A method of providing an ameliorating effect on the subjective symptoms and objective signs of a patient with heart failure comprising administering to said patient an effective amount of taurine.

2 Claims, No Drawings

METHOD OF AMELIORATING THE SUBJECTIVE SYMPTOMS AND OBJECTIVE SIGNS IN CONGESTIVE HEART FAILURE

BACKGROUND OF THE INVENTION

The present invention relates to a method for controlling the subjective symptoms and objective signs of heart failure.

Heart failure, the consequence of various types of heart disease, is one of the most common and serious disorders affecting individuals of all ages. It is the pathophysiological state in which the heart is not able to pump blood at a rate commensurate with the requirement of body tissues. Abnormality of cardiac function, frequently but not always caused by a defect in myocardial contraction, leads to a short supply with blood from the heart.

During the last few decades, increased knowledge of the physiological and biochemical mechanism in cardiac contraction has provided precise definition of heart failure state. Unfortunately, for many decades, there were few advances in treatment of heart failure, with treatments generally limited to restriction of physical activity and sodium intake, and administration of digitalis and diuretics as well as vasodilators, non-glycosides inotropic agents and metabolism-improving agents. Digitalis glycosides, which have been available for nearly 200 years, increase the force of contraction in both normal and failing heart muscle. However, they have a narrow therapeutic range, and dosages are commonly limited by the toxic side effect. Catecholamines exert a positive inotropic effect by activating cardiac $\beta_1$-receptors, but their usefulness is limited by their arrhythmogenic properties, short duration of action and a general requirement for parenteral administration. Other inotropic agents, such as glucagon, theophilline and imidazole have not been accepted for general clinical application in the treatment of heart failure. Furthermore, there are some patients who cannot be controlled by digitalis glycosides, even in combined use with other usual treatment modalities for heart failure.

Thus, there is a need for a new method for treating heart failure.

Taurine(2-aminoethanesulfonic acid), a non-toxic amino acid, has been shown to exert positive inotropic activity in guinea pigs (Dietrich, J & Diacono: Life Sci., 10: 499, 1971). Also shown is an increase in taurine levels in the left ventricles of patients dying of chronic congestive heart failure (Huxtable, R & Bressler, R: Science, 184: 1187, 1974). Taurine is a normal constituent of the human diet and usually taken about 50 to 150 mg per day per person. However, there previously has been no attempt to administer large doses of taurine for the treatment of heart failure.

DESCRIPTION OF THE INVENTION

It has been discovered that taurine effectively ameliorates the subjective symptoms and objective signs of heart failure, when administered to a patient with heart failure, without any adverse reaction.

Thus, according to the present invention, there is provided a method of providing an ameliorating effect on the subjective symptoms and objective signs of a patient with heart failure comprising administering an effective amount of taurine.

Taurine is effective by itself for some patients. However, when combined with the conventional therapeutic agents heretofore in use, it alters the effectiveness of treatment of heart failure favorably and decisively. Accordingly, in one preferred feature of the invention, taurine is administered together with conventional therapeutic agents heretofore in use, which include digitalis glycosides, diuretics, vasodilators, nonglycosides inotropic agents and others. Indeed, patients who have not been controllable or who have even worsened under prolonged administration of therapeutic agents heretofore in use for heart failure, have been unexpectedly improved with combined use of taurine. This shows that a method according to the invention makes it possible to improve the state of some patients showing the subjective symptons and objective signs of heart failure, which could not be expected with conventional therapeutic agents such as mentioned above.

Taurine may be administered in pure solid form. However, it is more conveniently administered as a pharmaceutical composition. Accordingly, in another preferred feature of the invention, taurine is administered as pharmaceutical compositions in the form of powders, granules, fine granules, capsules, tablets, solutions, syrups or any other conventional composition manufactured in the usual manner known in the art. Taurine may be administered orally, intravenously or by any other usual route, however, oral administration is preferred. Taurine may be administered in a daily dosage of 0.5 g to 12 g, divided into 2 to 4 doses. Thus, a pharmaceutical composition containing taurine used in the invention is preferably a dosage unit form for oral administration. Such a composition may contain one or more conventional therapeutic agents for heart failure in combination with taurine.

This invention is further illustrated, in the following experiments and examples.

EXPERIMENT 1

Acute Toxicity

Each of 10 Wistar male mice, weighing 16–18 g, was administered with 7 g/kg of taurine (as an aqueous solution of 100 ml/kg). During the period of 7 days after the administration of taurine, neither death nor behavioral changes were observed. When taurine was administrered intravenously, the same results were obtained.

EXPERIMENT 2

Clinical Study

Twenty-four patients with heart failure were administered every day, two doses containing 2 g each of taurine as granules, and then monitored. Results are shown in Table 1.

The underlying cause of heart failure and the combined therapeutic agents (+: combined, −: not combined) for each patient are shown in Table 2. The therapeutic agents combined with taurine were standard agents which have long been used. Most of the patients had not been improved or have been even worsened under the therapeutic agents in Table 2, prior to the new therapeutic modality of this invention being used. The severity of heart failure was expressed by NYHA Function Class (I to IV, mild to severe according to New York Heart Association) and a score based on observation of clinical symptoms and signs as shown in Table 3. The presence of a symptom or sign was given the point value indicated in the right column and the values for each of the symptoms and signs were summed up for the score. An increase in the score corresponds to a worsening in the patient's heart condition.

TABLE 1

| No | Age | Sex | Before NYHA | Before Score | After Week | After NYHA | After Score |
|---|---|---|---|---|---|---|---|
| 1 | 68 | M | II | 7.5 | 20 | I | 2 |
| 2 | 57 | M | II | 6.5 | 4 | II | 6.5 |
| 3 | 60 | F | IV | 13 | 8 | II | 5 |
| 4 | 67 | F | III | 12 | 32 | I | 2.5 |
| 5 | 48 | F | IV | 10 | 8 | II | 2.5 |
| 6 | 67 | M | III | 5 | 8 | II | 2.5 |
| 7 | 60 | F | III | 6 | 8 | II | 3 |
| 8 | 59 | M | III | 6 | 4 | III | 5 |
| 9 | 50 | M | II | 4 | 4 | II | 3 |
| 10 | 72 | F | III | 9.5 | 4 | II | 5 |
| 11 | 74 | M | III | 9.5 | 6 | II | 6 |
| 12 | 74 | M | II | 3.5 | 2 | II | 3.5 |
| 13 | 73 | M | III | 8.5 | 2 | III | 7.5 |
| 14 | 61 | M | II | 3.5 | 2 | II | 3 |
| 15 | 58 | F | II | 4.5 | 4 | II | 1 |
| 16 | 80 | F | III | 5 | 4 | II | 0.5 |
| 17 | 84 | F | III | 9 | 4 | II | 1 |
| 18 | 57 | F | III | 13 | 4 | II | 9 |
| 19 | 40 | M | II | 5.5 | 4 | II | 4.5 |
| 20 | 41 | M | III | 5 | 2 | II | 3 |
| 21 | 65 | M | III | 9.5 | 4 | II | 4 |
| 22 | 73 | M | II | 4.5 | 4 | II | 3 |
| 23 | 50 | F | II | 5.5 | 4 | II | 5.5 |
| 24 | 81 | F | III | 9 | 4 | II | 4 |

TABLE 2

| No | Underlying Cause | A | B | C |
|---|---|---|---|---|
| 1 | Mitral Stenosis & Regurgitation | + | − | − |
| 2 | Mitral Stenosis Aortic Stenosis & Regurgitation | + | + | − |
| 3 | Mitral Stenosis & Regurgitation Tricuspid Regurgitation | + | + | − |
| 4 | Mitral Stenosis & Regurgitation | + | + | + |
| 5 | Aortitis Syndorome | + | + | − |
| 6 | Chronic Cor Pulmonale | − | − | − |
| 7 | Mitral Stenosis & Regurgitation | + | + | − |
| 8 | Mitral Stenosis & Regurgitation Tricuspid Regurgitation | + | + | − |
| 9 | Aortic Stenosis & Regurgitation | − | − | − |
| 10 | Mitral Regurgitation | − | + | + |
| 11 | Chronic Cor Pulmonale | − | + | + |
| 12 | Ischemic Heart Disease | − | − | − |
| 13 | Ischemic Heart Disease | − | + | − |
| 14 | Hypertension | − | + | − |
| 15 | Ischemic Heart Disease | − | + | − |
| 16 | Aortic Regurgitation Mitral Regurgitation | + | + | + |
| 17 | Hypertension | + | + | − |
| 18 | Mitral Regurgitation | + | + | − |
| 19 | Ventricular Septal Defect | + | + | − |
| 20 | Ventricular Septal Defect | − | + | − |
| 21 | Chronic Cor Pulmonale Chronic Bronchitis | − | + | − |
| 22 | Aortic Stenosis & Regurgitation | − | + | − |
| 23 | Congestive Cardiomyopathy | − | − | − |
| 24 | Ischemic Heart Disease | + | + | − |

A: Digitalis,
B: Diuretics,
C: Vasodilators

TABLE 3

| Symptoms & Signs | Point Value |
|---|---|
| Orthopnea | 2 |
| Paroxysmal nocturnal dyspnea | 2 |
| Dyspnea on exertion | 1 |
| Fatigue | 1 |
| Anorexia, nausea or vomiting | 0.5 |
| Palpitation | 0.5 |
| Diastolic gallop rhythm | 2 |
| Pulsus alternans | 2 |
| Hepato-jugular reflux | 2 |

TABLE 3-continued

| Symptoms & Signs | Point Value |
|---|---|
| Pulmonary crackles | 2 |
| Neck vein distension | 1 |
| Hilar congestion | 1 |
| Cardiomegaly | 1 |
| Pleural effusion | 1 |
| Peripheral edema | 1 |
| Ascites | 1 |
| Decreased urinary output | 1 |
| Tachycardia | 0.5 |
| Weight gain | 0.5 |

EXAMPLE 1

Tablet

| | |
|---|---|
| Taurine | 500 g |
| Crystalline cellulose | 110 g |
| Carboxymethylcellulose calcium | 10 g |
| Light silicic anhydride | 10 g |
| Hydroxypropyl cellulose | 15 g |
| Magnesium stearate | 5 g |
| Total weight | 650 g |

Mixed homogeneously were the taurine, crystalline cellulose, carboxymethylcellulose calcium and light silicic anhydride. The resulting mixture was granulated with a solution of the hydroypropyl cellulose in isopropyl alcohol in a conventional manner. The granules thus obtained were mixed with the magnesium stearate, and tabletted using a 12 mm diameter punch to give tablets of 650 mg each.

EXAMPLE 2

Capsule 500 g of taurine and 5 g of magnesium stearate were homogeneously mixed. 505 mg each of the resulting mixture was filled into a No. 1 hard gellatin capsule.

EXAMPLE 3

Injectionable solution 20 g of taurine was dissolved in 400 ml of distilled water for injection and the resulting solution was sterilely filtered through a membrane filter. 20 ml each of the resulting solution was filled into an ampoule, sealed, and sterilized in autoclave to give an injectionable agent.

EXAMPLE 4

Granule

| | |
|---|---|
| Taurine | 1000 g |
| Lactose | 275 g |
| Hydroxypropyl cellulose | 25 g |
| Total weight | 1300 g |

The taurine and lactose were homogeneously mixed. The resulting mixture was granulated with a solution of the hydroxypropyl cellulose in isopropyl alcohol according in a conventional manner.

What I claim is:

1. A method of ameliorating at least one of the subjective symptoms and objective signs consisting of dyspnea, palpitation, hepato-jugular reflux, pulmonary crackles, cardiomegaly and peripheral edema in subjects who were clinically judged to have been in congestive heart failure which comprises administering to said subjects a therapeutically effective amount of taurine.

2. The method of claim 1 wherein the amount of taurine administered is from 0.5 g to 12 g per day.

* * * * *

UNITED STATES PATENT AND TRADEMARK OFFICE
CERTIFICATE OF CORRECTION

PATENT NO. : 4,565,830

DATED : January 21, 1986

INVENTOR(S) : Jun-ichi AZUMA

It is certified that error appears in the above—identified patent and that said Letters Patent is hereby corrected as shown below:

Column 3, in Table 2:

for "12 Ischemic Heart Disease" under Heading "A", "-" should be -- + --; and for "21 Chronic Cor Pulmonale" under Heading "C", "-" should be -- + --.

Signed and Sealed this

Second Day of September 1986

[SEAL]

Attest:

DONALD J. QUIGG

Attesting Officer     Commissioner of Patents and Trademarks